(12) United States Patent
Zweig et al.

(10) Patent No.: US 11,499,122 B2
(45) Date of Patent: Nov. 15, 2022

(54) METHODS FOR DEGREASING SURFACES

(71) Applicant: The Boeing Company, Chicago, IL (US)

(72) Inventors: Andrew Michael Zweig, Chesterfield, MO (US); Waynie Mark Schuette, Troy, IL (US); Carolyn L. Kupper, Summerville, SC (US)

(73) Assignee: The Boeing Company, Chicago, IL (US)

( * ) Notice: Subject to any disclaimer, the term of this patent is extended or adjusted under 35 U.S.C. 154(b) by 372 days.

(21) Appl. No.: 16/803,086

(22) Filed: Feb. 27, 2020

(65) Prior Publication Data

US 2021/0269751 A1    Sep. 2, 2021

(51) Int. Cl.
*C11D 7/30* (2006.01)
*C07C 21/18* (2006.01)

(52) U.S. Cl.
CPC ............... *C11D 7/30* (2013.01); *C07C 21/18* (2013.01)

(58) Field of Classification Search
CPC .............. C11D 7/5018; C11D 11/0023; C11D 11/0029; C11D 11/0047; C11D 3/245; C11D 3/43; C11D 17/0043; C11D 7/28; C11D 7/30

See application file for complete search history.

(56) References Cited

U.S. PATENT DOCUMENTS

| | | |
|---|---|---|
| 3,085,918 A | 4/1963 | Sherliker et al. |
| 6,176,942 B1 | 1/2001 | Clark et al. |
| 7,674,756 B2 | 3/2010 | Johnson et al. |
| 10,093,601 B2 | 10/2018 | Gregersen et al. |
| 10,479,747 B2 | 11/2019 | Gregersen et al. |
| 2007/0102021 A1* | 5/2007 | Nappa ............... C08J 9/0019 427/127 |
| 2007/0105738 A1 | 5/2007 | Nappa et al. |
| 2010/0004155 A1 | 1/2010 | Ishihara et al. |
| 2016/0326468 A1 | 11/2016 | Robin et al. |

FOREIGN PATENT DOCUMENTS

EP    2277983    1/2011

OTHER PUBLICATIONS

Search Report issued on EP Application 21157951.1, dated Jun. 28, 2021.
Fire Suppression Substitutes and Alternatives to Halon for U.S. Navy Applications, The National Academies Press, 111 pages, 1997.
(Continued)

*Primary Examiner* — John R Hardee
(74) *Attorney, Agent, or Firm* — Bell & Manning, LLC

(57) ABSTRACT

Methods for cleaning surfaces are provided. Such a method may comprise contacting a surface with a fluid comprising a compound of Formula I for a period of time; and removing the fluid from the surface, thereby providing a cleaned surface. Vapor phase degreasing systems for cleaning a surface of a component are also provided. Such a system may comprise a boil sump comprising liquid comprising a compound of Formula I; and a holder configured to hold a component in a vapor formed from the liquid.

17 Claims, 2 Drawing Sheets

(56) References Cited

OTHER PUBLICATIONS

Piotr A. Domanski, "From the Beginnings of Artificial Cold to Climate-Friendly Fluids; Evolution of Refrigerants Application," $9^{th}$ International Conference on Compressors and Refrigeration, China, Jul. 10, 2019.
Government of Canada Gazette, "Ozone-depleting substances," Modified Jul. 5, 2013.
Trichloroethylene (TCE); Regulation in Use in Vapor Degreasing Under TSCA Section 6(a), A Proposed Rule by the Environmental Protection Agency on /19/2017, published Jan. 19, 2017, 55 pages.
Ozone-Depleting Substances, United States Environmental Protection Agency official website, last updated on Jul. 31, 2018, 6 pages.
Chlorinated Solvents—he Key to Surface Cleaning Performance, HSIA, Jun. 2008, 12 pages.
Halotron BrX$^{tm}$ A High Performance Clean Fire Extinguishing Agent, Brochure published by American Pacific Corporation, 2017.
Chlorinated Solvents, Product Stewardship Manual, published by Olin, https://olinchlorinatedorganics.com/wp-conteni/uploads/2016/11/Chlorinated-Solvents-Product-Stewardship-Manual-Digital.pdf, available as of Feb. 18, 2020.

\* cited by examiner

METHODS FOR DEGREASING SURFACES

BACKGROUND

The manufacturing of components in various industries (e.g., automotive, aerospace, electronics) often leaves grease and oil on the surfaces of the components. Such contaminants interfere with subsequent surface treatments such as coating, painting, plating, and bonding the components with other materials. Therefore, various degreasing processes are used to clean the surfaces. Trichloroethylene (TCE) is a particularly effective degreasing agent, although alternatives such as trichloroethane and n-propyl bromide exist. However, degreasing processes which are more environmentally friendly would be useful.

SUMMARY

Provided herein are methods for cleaning surfaces. Vapor phase degreasing systems for carrying out the methods are also provided.

In one aspect, methods for cleaning surfaces are provided. In a first embodiment, such a method comprises (a) contacting a surface with a fluid comprising a compound of Formula I for a period of time; and (b) removing the fluid from the surface, thereby providing a cleaned surface. Compounds of Formula I include

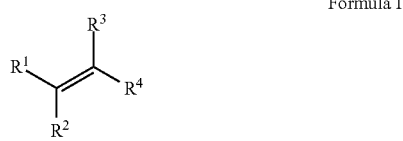

Formula I wherein $R^1$ is $-CR^5R^6R^7$ or $-CR^5R^6CR^8R^9R^{10}$;
$R^2$, $R^3$ and $R^4$ are each independently selected from halogen and hydrogen; and
$R^5$, $R^6$, $R^7$, $R^8$, $R^9$ and $R^{10}$ are each independently selected from halogen and hydrogen, wherein at least one of $R^5$, $R^6$, $R^7$, $R^8$, $R^9$ and $R^{10}$ is halogen;
wherein when $R^1$ is $-CR^5R^6CR^8R^9R^{10}$ and $R^8$, $R^9$ and $R^{10}$ are each F, then at least one of $R^2$, $R^3$ and $R^4$ is halogen;
wherein when $R^1$ is $-CR^5R^6CR^8R^9R^{10}$ and $R^8$, $R^9$ and $R^{10}$ are each F and when $R^2$ is Br, then one of $R^3$ and $R^4$ is halogen, or one of $R^5$ and $R^6$ is hydrogen; and
wherein when $R^1$ is $-CR^5R^6R^7$ and $R^5$, $R^6$, $R^7$ are each F, then $R^2$, $R^3$, and $R^4$ are independently selected from halogen and hydrogen.

In some embodiments according to the first embodiment, $R^1$ is $-CR^5R^6R^7$. In some such embodiments, $R^5$, $R^6$, $R^7$ are each a halogen and $R^2$, $R^3$ and $R^4$ are independently selected from hydrogen, Br, Cl and I. In other such embodiments, $R^5$, $R^6$, $R^7$ are each a halogen; $R^2$ is a halogen; and $R^3$ and $R^4$ are hydrogen. In other such embodiments, $R^5$, $R^6$, $R^7$ are each F; $R^2$ is a halogen; and $R^3$ and $R^4$ are hydrogen. In other such embodiments, the compound of Formula I is 2-bromo-3,3,3,-trifluoro-1-propene.

In some embodiments according to any of the above embodiments, the compound of Formula I is nonflammable.

In some embodiments according to any of the above embodiments, the compound of Formula I has a boiling point of greater than room temperature but less than 90° C.

In some embodiments according to any of the above embodiments, the fluid consists essentially of one or more compounds of Formula I, one or more stabilizers, and optionally, one or more compatibilizers.

In some embodiments according to any of the above embodiments, the fluid consists essentially of 2-bromo-3,3,3,-trifluoro-1-propene and one or more stabilizers.

In some embodiments according to any of the above embodiments, step (a) is carried out by exposing the surface to a vapor comprising the compound of Formula I and condensing the vapor on the surface.

In some embodiments according to any of the above embodiments, steps (a) and (b) are carried out using a vapor phase degreasing system comprising a liquid comprising the compound of Formula I. In some such embodiments, the method further comprises exposing the surface to a vapor comprising the compound of Formula I, the vapor formed from the liquid, and condensing the vapor on the surface. In other such embodiments, the compound of Formula I is 2-bromo-3,3,3,-trifluoro-1-propene.

In some embodiments according to any of the above embodiments, the surface is contaminated and the cleaned surface exhibits a reduced amount of contaminants as compared to the surface prior to cleaning. In some such embodiments, the contaminants are selected from a grease; an oil; a fat; a wax; a resin; a gum; a rosin; a substituted or unsubstituted hydrocarbon molecule, including fragments thereof; and combinations thereof.

In some embodiments according to any of the above embodiments, the surface is of an aerospace structure.

In some embodiments according to any of the above embodiments, the surface is of a component configured to deliver oxygen.

In another aspect, vapor phase degreasing systems for cleaning a surface of a component are provided. In a first embodiment, such a system comprises a boil sump comprising liquid comprising a compound of Formula I; and a holder configured to hold a component in a vapor formed from the liquid.

In some embodiments according to the first embodiment of the system, the compound of Formula I is 2-bromo-3,3,-trifluoro-1-propene.

In some embodiments according to any of the above embodiments of the system, the liquid consists essentially of one or more compounds of Formula I, one or more stabilizers, and optionally, one or more compatibilizers.

In some embodiments according to any of the above embodiments of the system, the liquid consists essentially of 2-bromo-3,3,3,-trifluoro-1-propene and one or more stabilizers.

Other principal features and advantages of the disclosure will become apparent to those skilled in the art upon review of the following drawings, the detailed description, and the appended claims.

BRIEF DESCRIPTION OF THE DRAWINGS

Illustrative embodiments of the disclosure will hereafter be described with reference to the accompanying drawings.

DETAILED DESCRIPTION

Figure 1:
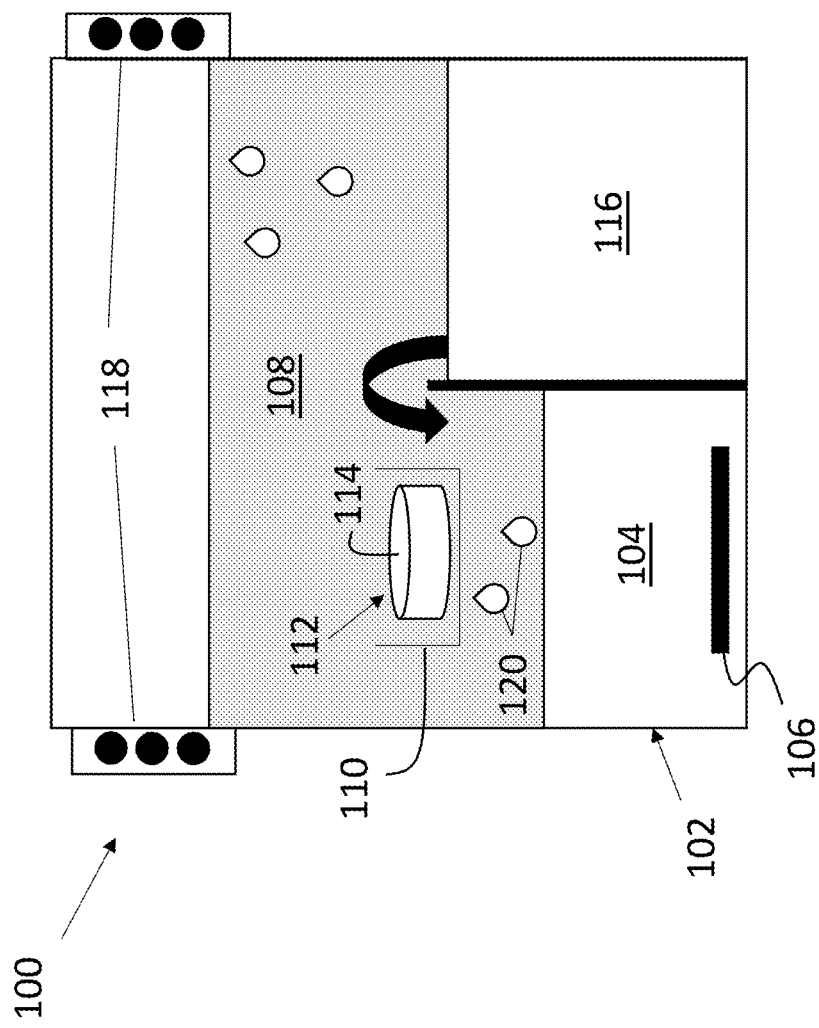
FIG. 1 depicts an illustrative vapor phase degreasing system which may be used to carry out the present methods.

The following is a list of definitions of terms and phrases used throughout the present disclosure.

The term "halogen" encompasses Cl, F, Br, and I.

The term "fluid" encompasses a gas, a liquid, and both. A fluid may comprise a single component, e.g., a single compound, or multiple components.

The term "dissolve" refers to incorporation into a liquid and encompasses partial dissolution, e.g., resulting in free or suspended particles, as well as complete dissolution.

The term "surface" in "surface to be cleaned" encompasses a surface which is, in fact, contaminated, as well as surfaces which may simply be suspected of being contaminated.

The term "nonflammable" means that the referenced material is tested according to the American Society for Testing and Materials (ASTM) G86 test, the ASTM D2512 test, or both such tests and that the material passes either or both such tests.

The phrase "ozone depletion potential" (ODP) is an index of the relative capability of a compound to destroy ozone as compared to CFCl$_3$ (ODP=1.00). The phrase "global warming potential" (GWP) is an index of the amount of warming emissions of a compound can produce over a period of 100 years as compared to CO$_2$ (GWP=1.00). ODP and GWP for a compound may be obtained or measured as described in Board, Naval Studies, and National Research Council. *Fire Suppression Substitutes and Alternatives to Halon for US Navy Applications*. National Academies Press, 1997.

The phrase "aerospace structure" may refer to any device, craft, machine, part or element used in the aerospace industry such as an aircraft such as an airplane; a rotocraft; a marine vehicle such as a submarine; a space vehicle such as a space ship; a trajectory device; drone; satellite; fuselage; wing; composite; and the like.

The phrase "automotive structure" may refer to any device, craft, machine, part or element used in the automotive industry.

The phrase "electronic structure" may refer to any device, circuit board, machine, part, element used in the electronics industry.

The present disclosure provides methods for cleaning a surface. In an embodiment, a method for cleaning a surface comprises contacting the surface with a fluid comprising a compound of Formula I for a period of time and removing the fluid from the surface, thereby providing a cleaned surface. Contaminants on the surface, if present, are removed along with the used fluid. Compounds of Formula I, further described immediately below, have been used as fire extinguishing agents. However, the present disclosure is based, at least in part, on the unexpected finding that compounds of Formula I, including 2-bromo-3,3,3,-trifluoro-1-propene (BTP), are able to remove a significant amount of contaminants, including greases and oils, from surfaces, including metal surfaces. These findings are described in the Example, below. In addition to their degreasing ability, fluids used in the present methods are, in embodiments, environmentally friendly and have the advantage of having a low ozone depletion potential and a low global warming potential as compared to existing degreasing agents such as TCE.

Compounds of Formula I include the following compounds:

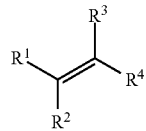

Formula I wherein $R^1$ is —$CR^5R^6R^7$ or —$CR^5R^6CR^8R^9R^{10}$;

$R^2$, $R^3$ and $R^4$ are each independently selected from halogen and hydrogen; and $R^5$, $R^6$, $R^7$, $R^8$, $R^9$ and $R^{10}$ are each independently selected from halogen and hydrogen, wherein at least one of $R^5$, $R^6$, $R^7$, $R^8$, $R^9$ and $R^{10}$ is halogen;

wherein when $R^1$ is —$CR^5R^6CR^8R^9R^{10}$ and $R^8$, $R^9$ and $R^{10}$ are each F, then at least one of $R^2$, $R^3$ and $R^4$ is halogen;

wherein when $R^1$ is —$CR^5R^6CR^8R^9R^{10}$ and $R^8$, $R^9$ and $R^{10}$ are each F and when $R^2$ is Br, then one of $R^3$ and $R^4$ is halogen, or one of $R^5$ and $R^6$ is hydrogen; and wherein when $R^1$ is —$CR^5R^6R^7$ and $R^5$, $R^6$, $R^7$ are each F, then $R^2$, $R^3$, and $R^4$ are independently selected from halogen and hydrogen.

In the above compounds: two or more substituents selected from $R^2$, $R^3$ and $R^4$ may be halogen; $R^2$, $R^3$ and $R^4$ may each be halogen; and/or $R^2$, $R^3$ and $R^4$ may each be independently selected from hydrogen, Br, Cl and I.

In the above compounds, $R^1$ may be —$CR^5R^6R^7$ in which case $R^5$, $R^6$ and $R^7$ may each be halogen or $R^5$, $R^6$, and $R^7$ may each be F.

In the above compounds, $R^1$ may be —$CR^5R^6CR^8R^9R^{10}$ in which case $R^8$, $R^9$ and $R^{10}$ may each be halogen; or $R^8$, $R^9$, and $R^{10}$ may each be F.

In the above compounds, $R^1$ may be —$CR^5R^6CR^8R^9R^{10}$ in which case $R^5$ and $R^6$ may each be halogen; or $R^5$ and $R^6$ may each be F.

In embodiments, the compound has Formula I and $R^1$ is —$CR^5R^6R^7$. In embodiments, the compound has Formula I and $R^1$ is —$CR^5R^6R^7$; $R^5$, $R^6$, $R^7$ are each a halogen; and $R^2$, $R^3$ and $R^4$ are independently selected from hydrogen, Br, Cl and I. In some such embodiments, $R^2$, $R^3$ and $R^4$ are independently selected from hydrogen, Br, and Cl. In embodiments, the compound has Formula I and $R^1$ is —$CR^5R^6R^7$; $R^5$, $R^6$, $R^7$ are each a halogen; $R^2$ is a halogen; and $R^3$ and $R^4$ are hydrogen. In embodiments, the compound has Formula I and $R^1$ is —$CR^5R^6R^7$, $R^5$, $R^6$, $R^7$ are each F; $R^2$ is a halogen; and $R^3$ and $R^4$ are hydrogen. In embodiments, the compound has Formula I and $R^1$ is —$CR^5R^6R^7$; $R^5$, $R^6$, $R^7$ are each F; $R^2$ is Br; and $R^3$ and $R^4$ are hydrogen. In each of these embodiments, the halogen may be a halogen other than I.

In embodiments, $R^1$ is —$CR^5R^6R^7$; $R^5$, $R^6$, $R^7$ are each F; $R^2$ is Br; and $R^3$ is halogen when $R^4$ is selected from hydrogen or Br, or $R^3$ is selected from hydrogen, Cl, Br or I when $R^4$ is F. In embodiments, $R^1$ is —$CR^5R^6R^7$; $R^5$, $R^6$, $R^7$ are each F; $R^2$ is I; and $R^3$ is halogen when $R^4$ is hydrogen, or $R^3$ is selected from hydrogen, F, Cl and I when $R^4$ is F.

In embodiments, the compound of Formula I is selected from 2-iodoperfluoro-1-butene; 2,3-dibromo-4,4,4-trifluoro-1-butene; 2-iodoperfluoro-1-butene; 2-bromoperfluoro-1-butene; 3-iodo-3,4,4,4-tetrafluoro-1-butene; 1-iodo-4,4,4-trifluoro-1-butene; 2-bromo-3,3,4,4,4-pentafluoro-1-butene; 1-bromo-4,4,4-trifluoro-1-butene;

2-chloro-3,3,4,4,4-pentafluoro-1-butene; 2-bromo-1,1,3,3,3-pentafluoropropene; 2-iodo-1,1,3,3,3-pentafluoropropene; 2-iodo-3,3,3-trifluoropropene; 2-bromo-3,3,3,-trifluoro-1-propene; isomers thereof; and combinations thereof. In embodiments, the compound of Formula I is 2-bromo-3,3,3,-trifluoro-1-propene.

The compounds of Formula I for use in the present methods are desirably those which are nonflammable. The nonflammability of the selected compound of Formula I may be confirmed via one or both of the following methods: ASTM G86 (Standard Test Method for Determining Ignition Sensitivity of Materials to Mechanical Impact in Ambient Liquid Oxygen and Pressurized Liquid and Gaseous Oxygen Environments) and ASTM D2512 (Standard Test Method for Compatibility of Materials with Liquid Oxygen). In order to be considered nonflammable, the selected compound of Formula I must pass one or both of these tests as set forth by the methods. For example, under ASTM G86, the selected compound of Formula I must show no reaction when being subjected to 20 successive impacts tests at 98 J or show only one reaction in 60 successive impact tests at 98 J. In embodiments, the compound of Formula I is nonflammable.

The compounds of Formula I for use in the present methods are, in embodiments, environmentally friendly and are desirably those which have a low ozone depletion potential (ODP) as well as a low global warming potential (GWP). In embodiments, the compound of Formula I has an ODP of no more than 0.1, 0.05, 0.005, 0.003, or 0.001. In embodiments, the compound of Formula I has a GWP of no more than 1.00, no more than 0.80, no more than 0.60, no more than 0.4, no more than 0.20, or no more than 0.15. BTP has an ODP of 0.0028 and a GWP of 0.26.

The compounds of Formula I for use in the present methods are generally liquids at room temperature (20° C. to 25° C.). In embodiments, the compound of Formula I has a boiling point of greater than room temperature but less than 90° C., less than 80° C., less than 70° C., less than 60° C., less than 50° C., or less than 40° C. BTP has a low boiling point of about 29° C. This is significantly lower than many of the degreasing agents used in vapor phase degreasing processes. Nevertheless, the Example, below, shows that BTP vapor is able to remove an unexpectedly large amount of aliphatic and aromatic hydrocarbons from a metal surface and thus, may be advantageously used in vapor phase degreasing processes despite its low boiling point.

Since they are generally liquids, the compounds of Formula I may be used by themselves in the present methods, but they may also be combined with additives such as a stabilizer. Stabilizers include compounds capable of scavenging an acid, scavenging a free radical, or both. Terpenes, such as limonene, are suitable stabilizers. Other illustrative stabilizers include p-cumene, β-pinene, vitamin E, beta-carotene, citral, citronellol, citronellal, para-cymeme, camphor, lanosterol, limonene, lutein, lycopene, menthadiene, menthol, myrcene, ocimene, oleanolic, dipentene, alpha-pinene, beta-pinene, phytol, sabinene, saponin, squalene, sylvestrene, terpinene, alpha-terpineol, terpinolene, turpentine, vitamin A, zingiberene, oleic acid, eleostearic acid, palmitoleic acid, linoleic acid, lincanic acid, petroselenic acid, abietic acid, linolenic acid, ricinoleic acid, and vaccenic acid. Combinations of different stabilizers may be used. In embodiments, the stabilizer is limonene. If present, these stabilizers may be included in an amount in a range of from 0.1 weight % to 4 weight % based on the total weight of the fluid. This includes an amount in a range of from 1 weight % to 4 weight % and from 2 weight % to 4 weight %. If more than one stabilizer is present, these amounts refer to the total amount of stabilizers.

Different types of compounds of Formula I may be used together in the methods, particularly those having similar boiling points. However, in embodiments, a single type of compound of Formula I is used. If more than one type of compound of Formula I is included in the fluid, a compatibilizer may be included as an additive. Compatibilizers include compounds capable of ensuring emulsification and preventing separation of different types of liquids. Illustrative compatibilizers include brominated vegetable oil, sucrose acetate isobutyrate, glycerol ester of wood rosin, and locust bean gum. Combinations of different compatibilizers may be used. In embodiments, the compatibilizer is brominated vegetable oil. If present, these compatibilizers may be included in an amount in a range of from 1 ppm to 10 ppm based on the total weight of the fluid. This includes an amount in a range of from 2 ppm to 10 ppm and from 5 ppm to 10 ppm. If more than one compatibilizer is present, these amounts refer to the total amount of compatibilizers.

In embodiments, the fluid comprises a compound of Formula I, a stabilizer, and optionally, a compatibilizer. In embodiments, the fluid comprises 2-bromo-3,3,3,-trifluoro-1-propene, a stabilizer, and optionally, a compatibilizer. In embodiments, the fluid consists essentially of, or consists of, one or more compounds of Formula I, one or more stabilizers, and optionally, one or more compatibilizers. In embodiments, the fluid consists essentially of, or consists of, 2-bromo-3,3,3,-trifluoro-1-propene and one or more stabilizers. In any of these embodiments, the stabilizer may be selected from terpenes. In any of these embodiments, the stabilizer may be limonene. If present, in any of these embodiments, the compatibilizer may be brominated vegetable oil.

Various techniques may be used to achieve contact of the surface to be cleaned with the fluid and subsequent removal of the used fluid. However, in embodiments, a vapor phase degreasing process is used. Such embodiments comprise exposing the surface to a vapor comprising a compound of Formula I, condensing the vapor on the surface, and removing the condensed vapor to provide the cleaned surface. The condensed vapor dissolves contaminants on the surface, if present. The condensed vapor may be removed from the surface, e.g., via gravity. Various vapor phase degreasing systems may be used to carry out these steps. The vapor may be formed from a liquid comprising the compound of Formula I. Stabilizers and/or compatibilizers may be included in the liquid as described above.

A schematic of an illustrative such vapor phase degreasing system 100 is shown in FIG. 1. The system 100 includes a boil sump 102 configured to contain a liquid 104 comprising the compound of Formula I. The boil sump 102 includes a heater 106 to heat the liquid 104 to provide a vapor 108, also comprising the compound of Formula I. The system 100 further includes a holder 110 configured to hold a component 112 having the surface 114 to be cleaned. The illustrative system 100 further includes a rinse sump 116 and a cold trap 118. During operation, the relatively hot vapor 108 condenses on the relatively cold surface 114 of the component 112. The condensed vapor 120, including any contaminants dissolved herein, may drip off the surface 114 back into the boil sump 102. Escaping hot vapor 108 condenses via the cold trap 118 and drips into the rinse sump 116, which may be recovered and reused continuously. Various conditions such as the temperature of boil sump 102, the placement of the holder 110, the length of exposure (i.e., period of time), etc. may be adjusted depending upon considerations such as the selected compound of Formula I, the material/dimensions/weight of the component, the nature of the contaminant(s), etc. In embodiments, the vapor phase degreasing system 100 is a closed top system.

In embodiments, the method is carried out via a vapor phase degreasing process as described above in which the vapor is formed from a liquid comprising a compound of Formula I, a stabilizer, and optionally, a compatibilizer. In embodiments, the liquid comprises 2-bromo-3,3,3,-trifluoro-1-propene, a stabilizer, and optionally, a compatibilizer. In embodiments, the liquid consists essentially of, or consists of, one or more compounds of Formula I, one or more stabilizers, and optionally, one or more compatibilizers. In embodiments, the liquid consists essentially of, or consists of, 2-bromo-3,3,3,-trifluoro-1-propene and one or more stabilizers. In any of these embodiments, the stabilizer may be selected from terpenes. In any of these embodiments, the stabilizer may be limonene. If present, in any of these embodiments, the compatibilizer may be brominated vegetable oil.

It is to be understood that FIG. 1 is merely illustrative and other vapor phase degreasing systems may be used which may have fewer, additional, and/or different components as shown in FIG. 1, e.g., a water separator, a sonicator, a vacuum pump, etc. The type of vapor phase degreasing system is not particularly limiting.

The present methods may be carried out using other techniques to achieve contact of the surface to be cleaned with the fluid, including spraying, wiping, immersing, dipping, etc. These techniques may also be achieved with the vapor phase degreasing system 100 of FIG. 1. For example, the surface 114 to be cleaned may be exposed to the vapor 108 comprising the compound of Formula I as described above and/or immersed directly into the liquid 104 in the boil sump 102. Spraying the surface 114 with the vapor 108 or with the liquid 104 may also be used.

The surfaces which may be cleaned by the present methods are not particularly limited. By way of illustration, the surface may be a metal surface, a polymeric surface, a glass surface, a semiconductor surface, a ceramic surface, or a composite thereof. Metal surfaces include, e.g., surfaces of aluminum, magnesium, titanium, zinc, brass, steel, and alloys thereof. The surfaces may ones of a structure such as an aerospace structure, an automotive structure, or an electronic structure. In embodiments, the surface of a component configured to deliver $O_2$ or an $O_2$-containing gas such as air. Such a component may be $O_2$ tubing, hosing, and the like.

The present methods may be used to remove a variety of contaminants from the surfaces described herein. However, the methods are particularly useful for removing contaminants such as greases, oils, fats, waxes, resins, gums, rosins, as well as other (substituted or unsubstituted) hydrocarbon molecules and/or fragments thereof. Thus, in embodiments, the contaminants are selected from a grease; an oil; a fat; a wax; a resin; a gum; a rosin; a substituted or unsubstituted hydrocarbon molecule, including fragments thereof and combinations thereof. The contaminants may be derived from materials used for lubricating during a variety of manufacturing processes such as substrate (e.g., metal) cutting, bending, and forming. The contaminants may be derived from materials used as mold release agents. Illustrative contaminants include polybutenes and polyisobutenes. The Example, below, demonstrates that a variety of aliphatic and aromatic hydrocarbons are removed from a metal surface coated with a corrosion inhibiting composition after exposure to a vapor comprising BTP.

Confirmation that the present methods are able to clean a desired surface, as well as quantification of the amount of contaminants removed from the surface may be carried out by measuring the mass of a component having the desired surface before and after carrying out the present methods. Such quantification is demonstrated in the Example, below. In embodiments, the cleaned surface exhibits a reduced amount of contaminants as compared to the surface prior to cleaning, e.g., as evidenced by a loss of mass. FTIR may also be carried out to identify the contaminants removed, as demonstrated in the Example, below. Another technique to confirm contamination removal involves exposing the desired surface to a solvent such as hexane, recovering the solvent, performing FTIR analysis on a portion of the recovered solvent to identify soluble contaminants, and evaporating a remaining portion of the recovered solvent to identify insoluble contaminants. This may be carried out on the desired surface before and after cleaning.

Example

Samples of aluminum alloy coupons (2024-T3) coated with a commercially available corrosion inhibiting composition (BMS 3-23 Ardrox AV-8 Ty II Class II, Grade A) were placed in a Parr non-stirred reactor along with a large glass tube containing 2-bromo-3,3,3,-trifluoro-1-propene (BTP). Coupons were 4"×6"×0.060". The corrosion inhibiting composition is a blend of several materials including hydrotreated heavy naphtha; naphtha (petroleum), light steam-cracked, debenzenized, polymers; organic acid and barium soap; calcium dinonylnaphthalene sulfonate; lanolin; aliphatic mineral spirits; and cyclohexanone. A coating of the corrosion inhibiting composition is formed by spraying to achieve a continuous, bubble-free coating after drying. The reactor was sealed, evacuated to 15 mm Hg, and then allowed to equilibrate to atmospheric pressure by the evaporation of BTP, which has significant vapor pressure at 73° F. Samples were exposed for 24 hours, then the reactor was opened and vented. The mass loss of the coating on each coupon was determined from the known mass of the coating before BTP exposure and the mass change in the coating calculated by measuring the mass of the coupon before and after BTP exposure. The results are shown in Table 1 below. The average or mean value is reported as is the standard deviation (abbreviated as Std. Dev.).

TABLE 1

Mass Loss in Coating on Coupons After Exposure to BTP.

| Coupon | Mass of coupon before exposure (g) | Mass of coupon after exposure (g) | Mass change in coupon (g) | Mass of coating before exposure (g) | Mass loss of coating (%) |
|---|---|---|---|---|---|
| A6 | 69.623 | 69.330 | 0.293 | 0.401 | 73 |
| A7 | 69.659 | 69.363 | 0.296 | 0.401 | 74 |
| A8 | 69.316 | 68.940 | 0.376 | 0.401 | 94 |
| A9 | 69.397 | 69.042 | 0.355 | 0.401 | 89 |
| A10 | 69.535 | 69.205 | 0.330 | 0.401 | 82 |
| Mean | | | 0.330 | | 82% |
| Std. Dev. | | | 0.36 | | 9% |

These results show that the BTP vapor resulted in a remarkable loss of material from the coating of the coupon. In fact, much of the coating softened and dripped off the metal surface after BTP exposure, covering the holder and the bottom of the reactor vessel.

Figure 2:
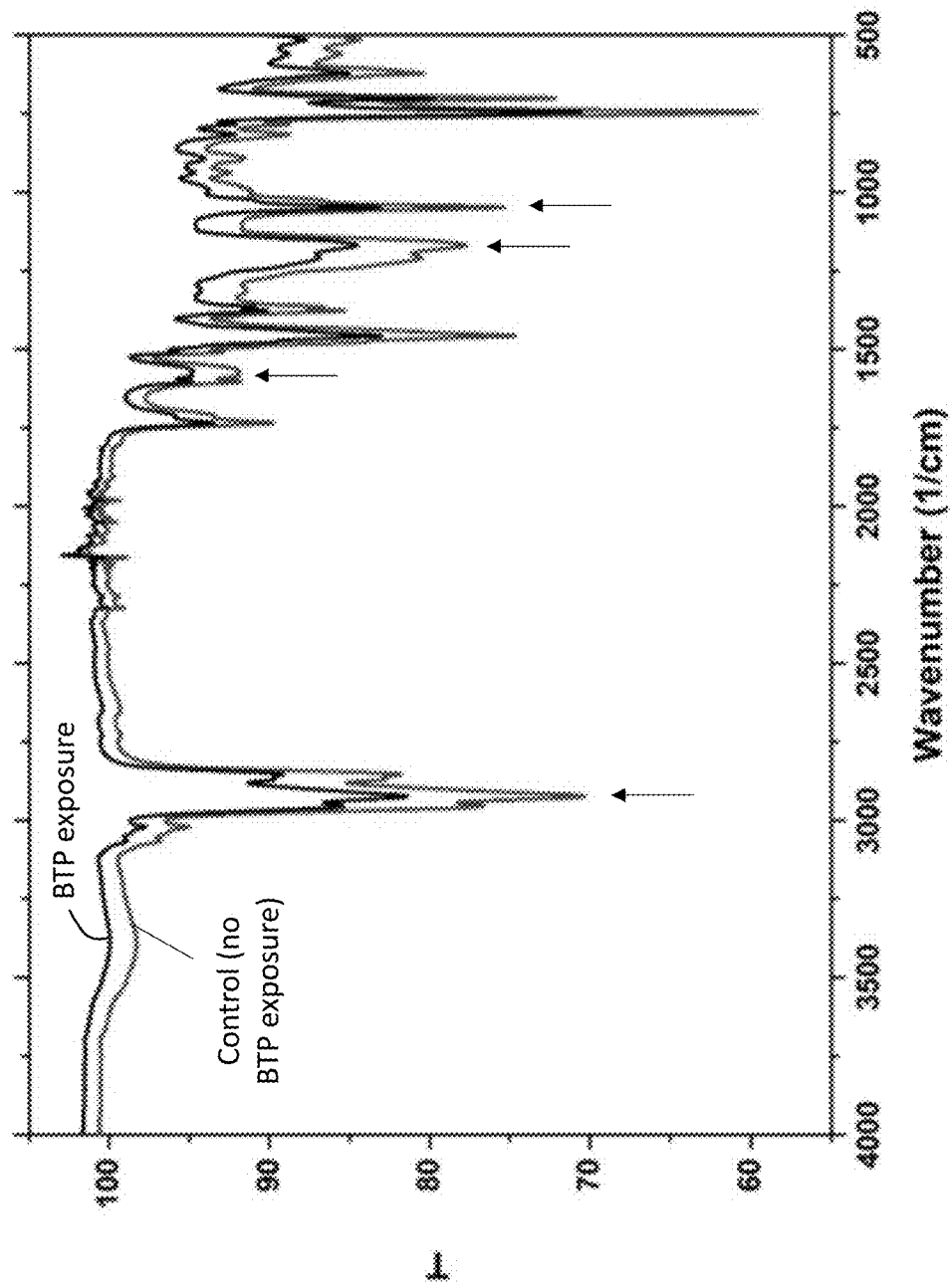
FIG. 2 shows Fourier Transform Infrared Spectroscopy (FTIR) spectra for a coated metal (aluminum alloy) surface after exposure to 2-bromo-3,3,3,-trifluoro-1-propene (BTP) and for a control coated metal surface (no BTP exposure). The coating on the metal surface was a corrosion inhibiting composition including grease and oil components. The FTIR spectra for the BTP-exposed surface shows loss of aliphatic and aromatic species (decreased intensities at the wavelengths indicated with arrows), consistent with the loss of such grease and oil components from the coating.

FTIR spectra were collected in order to assess the type of material being removed from the coating. Specifically, FTIR spectra were obtained for sample A-09 (after BTP exposure) and for control sample A-11 (no BTP exposure). As shown in FIG. 2, the BTP-exposed sample A-09 showed decreased peak intensities at 2900 $cm^{-1}$ and 1200 $cm^{-1}$, suggesting a loss of aliphatic materials from the coating. Decreased peak intensities were also observed at 1600 $cm^{-1}$ and 1040 $cm^{-1}$, suggesting a loss of aromatic materials from the coating.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more."

The foregoing description of illustrative embodiments of the disclosure has been presented for purposes of illustration and of description. It is not intended to be exhaustive or to limit the disclosure to the precise form disclosed, and modifications and variations are possible in light of the above teachings or may be acquired from practice of the disclosure. The embodiments were chosen and described in order to explain the principles of the disclosure and as practical applications of the invention to enable one skilled in the art to utilize the disclosure in various embodiments and with various modifications as suited to the particular use contemplated. It is intended that the scope of the disclosure be defined by the claims appended hereto and their equivalents.

What is claimed is:

1. A method for cleaning a surface, the method comprising:
   (a) contacting a surface with a fluid consisting of 2-bromo-3,3,3,-trifluoro-1-propene and optionally, one or both of a stabilizer and a compatibilizer, for a period of time; and
   (b) removing the fluid from the surface, thereby providing a cleaned surface.

2. The method of claim 1, wherein step (a) is carried out by exposing the surface to a vapor formed from the fluid and condensing the vapor on the surface.

3. The method of claim 1, wherein steps (a) and (b) are carried out using a vapor phase degreasing system comprising a liquid consisting of the 2-bromo-3,3,3,-trifluoro-1-propene and optionally, one or both of the stabilizer and the compatibilizer.

4. The method of claim 3, further comprising exposing the surface to a vapor formed from the liquid, and condensing the vapor on the surface.

5. The method of claim 3, wherein the fluid consists of the 2-bromo-3,3,3,-trifluoro-1-propene and the stabilizer.

6. The method of claim 3, wherein the fluid consists of the 2-bromo-3,3,3,-trifluoro-1-propene.

7. The method of claim 1, wherein the surface is contaminated and the cleaned surface exhibits a reduced amount of contaminants as compared to the surface prior to cleaning.

8. The method of claim 7, wherein the contaminants are selected from a grease; an oil; a fat; a wax; a resin; a gum; a rosin; a substituted or unsubstituted hydrocarbon molecule, including fragments thereof; and combinations thereof.

9. The method of claim 1, wherein the surface is of an aerospace structure.

10. The method of claim 1, wherein the surface is of a component configured to deliver oxygen.

11. The method of claim 1, wherein the fluid consists of the 2-bromo-3,3,3,-trifluoro-1-propene, the stabilizer, and optionally, the compatibilizer.

12. The method of claim 1, wherein the fluid consists of the 2-bromo-3,3,3,-trifluoro-1-propene and the stabilizer.

13. The method of claim 1, wherein the fluid consists of the 2-bromo-3,3,3,-trifluoro-1-propene.

14. A vapor phase degreasing system for cleaning a surface of a component, the system comprising:
   a boil sump comprising liquid consisting of 2-bromo-3,3,3,-trifluoro-1-propene and optionally, one or both of a stabilizer and a compatibilizer; and
   a holder configured to hold a component in a vapor formed from the liquid.

15. The system of claim 14, wherein the liquid consists of the 2-bromo-3,3,3,-trifluoro-1-propene, the stabilizer, and optionally, the compatibilizer.

16. The system of claim 14, wherein the liquid consists of the 2-bromo-3,3,3,-trifluoro-1-propene and the stabilizer.

17. The system of claim 14, wherein the liquid consists of the 2-bromo-3,3,3,-trifluoro-1-propene.

* * * * *